(12) United States Patent
Yardimci et al.

(10) Patent No.: US 8,033,157 B2
(45) Date of Patent: Oct. 11, 2011

(54) MEDICAL FLUID AIR BUBBLE DETECTION APPARATUS AND METHOD

(75) Inventors: Atif M. Yardimci, Vernon Hills, IL (US); Serhan Acikgoz, Des Plaines, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 370 days.

(21) Appl. No.: 11/865,565

(22) Filed: Oct. 1, 2007

(65) Prior Publication Data

US 2009/0088687 A1 Apr. 2, 2009

(51) Int. Cl.
*G01N 7/00* (2006.01)
(52) U.S. Cl. ........................................ 73/19.01
(58) Field of Classification Search ............... 73/19.1
See application file for complete search history.

(56) References Cited

U.S. PATENT DOCUMENTS

| | | | |
|---|---|---|---|
| 2,755,662 A | 7/1956 | Swengel | |
| 2,885,887 A | 5/1959 | Hanysz | |
| 2,949,769 A | 8/1960 | Heller | |
| 3,223,298 A * | 12/1965 | Roberson et al. | 222/541.6 |
| 3,392,574 A | 7/1968 | Lemon et al. | |
| 3,443,433 A | 5/1969 | Liston et al. | |
| 3,633,590 A * | 1/1972 | Pocock et al. | 73/37.7 |
| 3,641,994 A | 2/1972 | Gosling et al. | |
| 3,648,694 A | 3/1972 | Mogos et al. | |
| 3,881,353 A | 5/1975 | Fathauer | |
| 3,898,637 A * | 8/1975 | Wolstenholme | 340/606 |
| 3,914,984 A | 10/1975 | Wade | |
| 3,921,622 A | 11/1975 | Cole | |
| 3,974,681 A | 8/1976 | Namery | |
| 3,974,683 A | 8/1976 | Martin | |
| 3,997,420 A | 12/1976 | Buzza | |
| 4,014,206 A | 3/1977 | Taylor | |
| 4,015,464 A | 4/1977 | Miller et al. | |
| 4,022,058 A | 5/1977 | Brown | |
| 4,068,521 A | 1/1978 | Cosentino et al. | |
| 4,102,655 A | 7/1978 | Jeffery et al. | |
| 4,112,773 A | 9/1978 | Abts | |
| 4,121,094 A | 10/1978 | DeVito et al. | |
| 4,122,713 A | 10/1978 | Staaz et al. | |
| 4,137,940 A | 2/1979 | Faisandier | |
| 4,202,049 A | 5/1980 | Wetzel | |
| 4,341,116 A | 7/1982 | Bilstad et al. | |
| 4,358,423 A | 11/1982 | Nedetsky | |
| 4,418,565 A | 12/1983 | St. John | |
| 4,487,601 A | 12/1984 | Lindemann | |
| 4,607,520 A * | 8/1986 | Dam | 73/19.03 |
| 4,651,555 A | 3/1987 | Dam | |
| 4,666,598 A | 5/1987 | Heath et al. | |

(Continued)

FOREIGN PATENT DOCUMENTS

EP 0484876 5/1992

(Continued)

*Primary Examiner* — Hezron E Williams
*Assistant Examiner* — Alex Devito
(74) *Attorney, Agent, or Firm* — K&L Gates LLP

(57) ABSTRACT

A medical fluid air detection apparatus includes an emitter, a receiver, a housing configured to hold at least a portion of a medical fluid conduit between the emitter and the receiver, where the medical fluid conduit includes a narrowed inner diameter at the medical fluid conduit portion that forces flow of medical fluid through the narrowed diameter, and where the narrowed diameter is configured to enhance operation of the emitter and the receiver.

19 Claims, 4 Drawing Sheets

U.S. PATENT DOCUMENTS

| | | | |
|---|---|---|---|
| 4,673,927 | A | 6/1987 | Cianciavicchia et al. |
| 4,681,606 | A | 7/1987 | Swan et al. |
| 4,722,224 | A | 2/1988 | Scheller et al. |
| 5,026,348 | A | 6/1991 | Venegas |
| 5,092,980 | A | 3/1992 | Maurer et al. |
| 5,177,993 | A | 1/1993 | Beckman et al. |
| 5,191,795 | A | 3/1993 | Fellingham et al. |
| 5,205,153 | A * | 4/1993 | Hlavinka et al. ............. 73/19.03 |
| 5,284,568 | A | 2/1994 | Pace et al. |
| 5,394,732 | A | 3/1995 | Johnson et al. |
| 5,451,373 | A | 9/1995 | Lewis et al. |
| 5,455,423 | A * | 10/1995 | Mount et al. .................. 250/343 |
| 5,462,256 | A * | 10/1995 | Minick et al. .................. 251/331 |
| 5,489,265 | A * | 2/1996 | Montalvo et al. ............. 604/67 |
| 5,537,853 | A | 7/1996 | Finburgh et al. |
| 5,583,280 | A | 12/1996 | Mo et al. |
| 5,631,552 | A | 5/1997 | Ogawa et al. |
| 5,690,831 | A | 11/1997 | Kenley et al. |
| 5,723,773 | A | 3/1998 | Bryan |
| 6,142,008 | A | 11/2000 | Cole et al. |
| 6,223,588 | B1 | 5/2001 | Burgass et al. |
| 6,284,142 | B1 | 9/2001 | Muller |
| 6,457,346 | B1 | 10/2002 | Kline-Schoder et al. |
| 6,572,576 | B2 | 6/2003 | Brugger et al. |
| 6,616,633 | B1 | 9/2003 | Butterfield et al. |
| 6,723,216 | B2 | 4/2004 | Taagaard et al. |
| 6,730,267 | B2 | 5/2004 | Stringer et al. |
| 6,773,670 | B2 | 8/2004 | Stringer et al. |
| 6,804,991 | B2 | 10/2004 | Balschat et al. |
| 6,843,099 | B2 | 1/2005 | Derek et al. |
| 6,960,322 | B2 | 11/2005 | Stringer et al. |
| 6,969,865 | B2 | 11/2005 | Duchon et al. |
| 7,040,142 | B2 | 5/2006 | Burbank |
| 7,087,033 | B2 | 8/2006 | Brugger et al. |
| 7,141,037 | B2 | 11/2006 | Butterfield et al. |
| 7,194,919 | B2 | 3/2007 | Shkarlet et al. |

FOREIGN PATENT DOCUMENTS

| | | |
|---|---|---|
| JP | 107756 | 5/1991 |
| JP | 107758 | 5/1991 |
| SU | 838552 | 6/1981 |
| WO | 9641156 | 12/1996 |
| WO | 9837402 | 8/1998 |

* cited by examiner

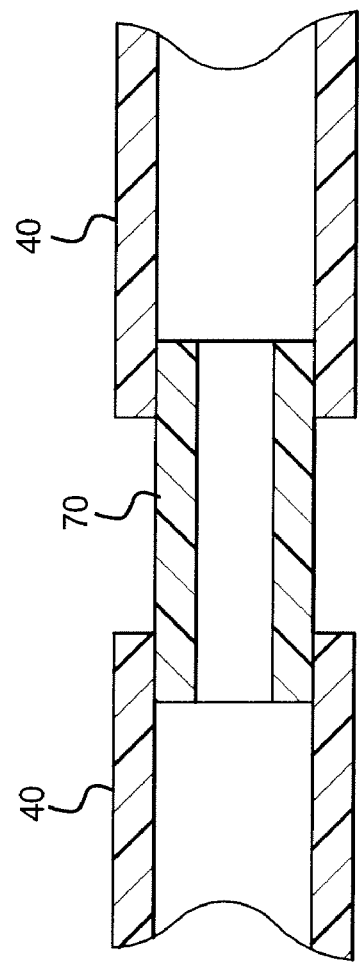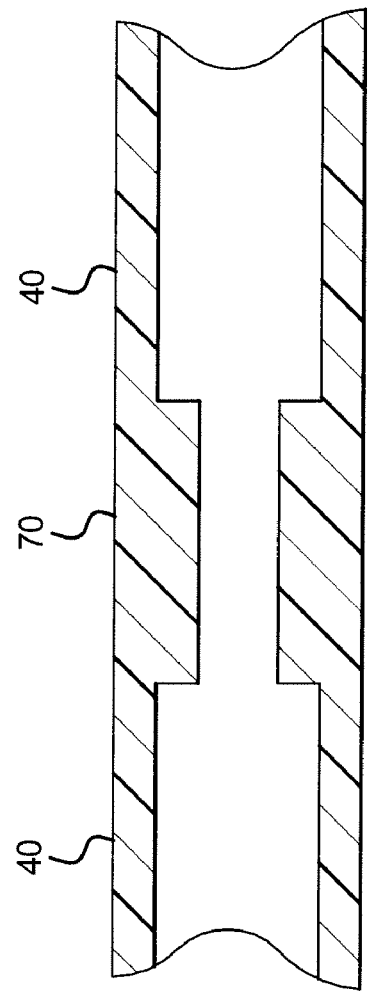

MEDICAL FLUID AIR BUBBLE DETECTION APPARATUS AND METHOD

BACKGROUND

The examples discussed below relate generally to medical fluid delivery. More particularly, the examples disclose systems, methods and apparatuses for dialysis such as hemodialysis ("HD") automated peritoneal dialysis ("APD").

Due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate to cause diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that a patient receiving more frequent treatments removes more toxins and waste products than a patient receiving less frequent but perhaps longer treatments. A patient receiving more frequent treatments does not experience as much of a down cycle as does an in-center patient who has built-up two or three days worth of toxins prior to a treatment. In certain areas, the closest dialysis center can be many miles from the patient's home, causing door-to-door treatment time to consume a large portion of the day. HHD can take place overnight or during the day while the patient relaxes, works or is otherwise productive.

Another type of kidney failure therapy is peritoneal dialysis which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain to allow spent dialysate fluid to drain from the peritoneal cavity. The patient then colmects the catheter to a bag of fresh dialysate to infuse fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter and into the patient's peritoneal cavity. APD machines also allow for the dialysate to dwell within the cavity and for the transfer of waste, toxins and excess water to take place. The source can include multiple sterile dialysate solution bags.

APD machines pump spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities, entrained air is a concern. Entrained air can cause inaccuracies when pumping dialysate for either PD or HD. Entrained air entering a patient's peritoneum during PD can cause discomfort. Entrained air entering a patient's bloodstream during HD can have severe consequences. Sensors exist to detect air flowing through medical tubing, however, certain sensors have problems detecting small air bubbles, e.g., about 400 microns. Accordingly, a need exists to provide an apparatus and method for detecting entrained air, especially small bubbles of air, in a line running to or from a patient, so that corrective action can be taken.

SUMMARY

The present disclosure relates to an air detection apparatus and method, which are applicable to any medical fluid delivery system. The embodiments discussed below, however, are directed generally to dialysis, such as hemodialysis ("HD") and peritoneal dialysis ("PD"), for detecting air entrained in blood or dialysate (or a component thereof). It should be kept in mind when reading this disclosure however that the principles disclosed herein have broader application than just the dialysis field.

One type of air detector or sensor that can be used with the present apparatus and method is an acoustical or ultrasound detector. The ultrasound detector uses a transmitter to send an ultrasonic sound wave through a mechanically coupled flexible tube through which the medical fluid flows. A receiver collects the transmitted acoustical wave. The transmitter and receiver can for example be piezo-based transducers. A change in the transmission of the acoustical wave is interpreted by a controller of a system using the detector (e.g., dialysis instrument having processing and memory) as a "break" in the fluid path. Air bubbles passing through the tube cause the break due to a corresponding high impedance mismatch. The smaller the bubbles, however the smaller the impedance mismatch. Bubbles that are too small may not create enough impedance mismatch to trip the controller monitoring the detector's signal.

The present apparatus and method increases an effective tubing thickness and decreases an inner diameter of a tube carrying patient fluid at an area at which the ultrasonic detector is operating with the tube. In one embodiment, a smaller tube is placed inside a patient tube. The outer diameter of the smaller tube is the same size or even slightly bigger than the inner diameter of the patient tube for a press or interference fit. The apparatus increases the ability of the ultrasonic detector to sense smaller air bubbles. It is contemplated to increase sampling rates and increase recording lengths in addition to using the above apparatus to further increase the ability to detect smaller air bubbles.

Accordingly, in one embodiment, a medical fluid air detection apparatus includes an emitter, a receiver, a housing configured to hold at least a portion of a medical fluid conduit between the emitter and the receiver where the medical fluid conduit includes a narrowed inner diameter at the portion, forcing flow of medical fluid through the narrowed portion to enhance operation of the emitter and the receiver.

The emitter and receiver operate acoustically in the ultrasonic frequency range in one embodiment.

The housing that holds the portion of the conduit can be attached to a medical fluid delivery instrument, such as a dialysis instrument. The housing is alternatively a housing of a medical fluid, e.g., dialysis instrument. The housing is further alternatively a stand-alone housing. In any case, the housing can include a retainer or mechanical holding device that releasably grasps and holds the medical fluid conduit.

In one embodiment, the medical fluid conduit is a tube. The narrowed portion is formed via an obstruction which effectively increases a wall thickness of the medical fluid conduit. The obstruction can be wedged into the tube at the portion of the medical fluid conduit. The obstruction can be a small tube sized to press-fit inside the medical fluid conduit. The obstruction can have a cross-sectional area that consumes at least 75% percent of a cross-sectional area of the portion of the medical fluid conduit. The obstruction can likewise include an inner diameter that is at least 50% percent less than an inner diameter of the medical fluid conduit.

Alternatively, the narrowed portion is produced via a smaller tube which is configured to seal to a larger tube at one or both ends. The smaller tube is held by the housing.

Further alternatively, the portion of the medical fluid conduit is a portion of a medical fluid pumping cassette where the conduit is a to-patient conduit extending from the pumping cassette. The portion is narrowed with respect to the to-patient conduit. The narrowed portion can have thickened walls relative to the to-patient conduit or walls of the same thickness as shown in more detail below.

The medical fluid conduit can reside in the pumping cassette such that the housing is a housing of a dialysis instrument which is configured to accept the cassette. Here, the conduit can be a to-patient conduit residing within the medical fluid pumping cassette where the portion is a portion of the to-patient conduit.

Still further alternatively, the conduit can be a first conduit and the emitter and receiver can be a first emitter and a first receiver. The air detection apparatus also includes a second conduit, a second emitter and second receiver where the second conduit also includes a narrowed portion configured to force medical fluid to flow through the narrowed portion to improve operation with the second emitter and the second receiver. The first conduit can be a medical fluid supply conduit, while the second conduit is a to-patient conduit.

In another embodiment, a medical fluid air detection apparatus includes an air detection sensor and a medical fluid conduit including a narrowed inner diameter configured to force medical fluid to flow through the narrowed inner diameter at a portion of the conduit operating with the sensor. Here, at least one of: (i) the sensor is an ultrasonic sensor; (ii) the sensor includes an emitter and a receiver; and (iii) the apparatus includes a housing configured to hold the medical fluid conduit adjacent to the sensor. As discussed, the medical fluid conduit can include an internal obstruction at the portion that forms the narrowed inner diameter.

In one method of the present disclosure, air detection is improved by forcing a medical fluid to flow within a narrowed portion of a medical fluid conduit, and detecting air within the medical fluid flowing through the narrowed portion. The method further includes enhancing an ability of a sensor performing the air detecting to detect air bubbles of a diameter less than one millimeter by forcing the medical fluid through the narrowed portion. Further, the method includes contacting an internal surface of the medical fluid conduit with a smaller diameter conduit to create the narrowed portion. Air detection can be further enhanced by increasing detector sample rates.

It is accordingly an advantage of the present disclosure to improve medical fluid air detection.

It is another advantage of the present disclosure to improve medical fluid air detection of smaller sized air bubbles.

Additional features and advantages are described herein, and will be apparent from, the following Detailed Description and the figures.

BRIEF DESCRIPTION OF THE FIGURES

FIGS. 3A and 3B illustrate different ways to reduce the inner diameter of the conduit carrying the medical fluid to be sensed.

DETAILED DESCRIPTION

Figure 1:
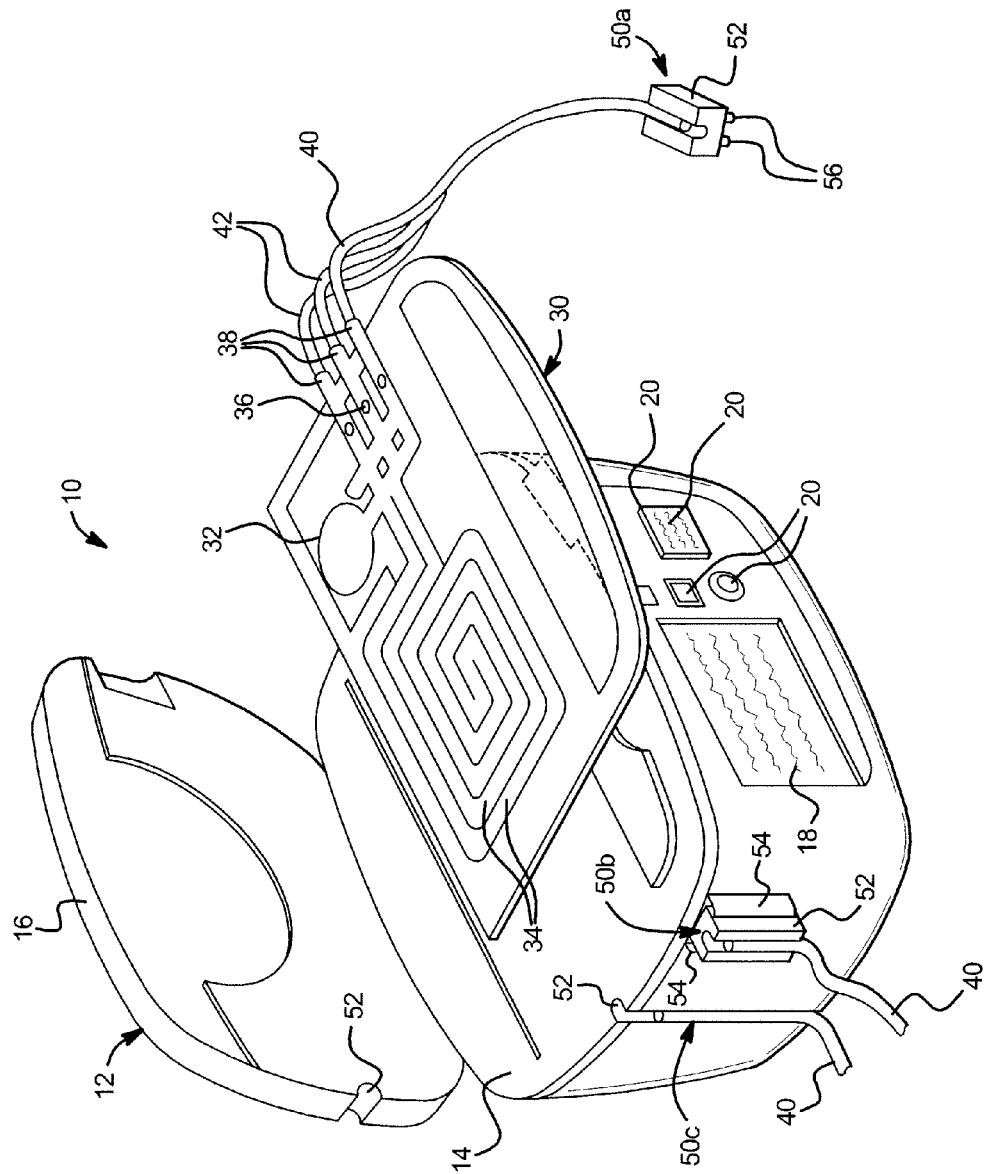
FIG. 1 is a perspective view of a medical fluid system, such as a dialysis system, that can employ the air sensing apparatus and method in a plurality of different ways.

Referring now to the drawings and in particular to FIG. 1, medical fluid system 10 portable with the air detection apparatus and method of the present disclosure is illustrated. The air detection apparatus and method are applicable to many different types of medical fluid delivery systems, such as drug delivery systems. The embodiments described herein however relate generally to dialysis, such as a blood based dialysis including hemodialysis ("HD"), hemofiltration ("HF"), hemodiafiltration ("HDF") and peritoneal dialysis systems ("PD"). Each dialysis modality includes a dialysate or infusate which is delivered either directly to a patient's peritoneum, blood system or dialyzer. That fluid can become entrained with air, which can be problematic for the therapy or for the patient as mentioned above. Moreover, in blood systems air can become entrained in the patient's blood, potentionally causing serious problems for the patient. Thus, it is contemplated to use the air detection apparatus and method to detect air in both blood and dialysate (including components of dialysate and replacement fluid for HF). System 10 of FIG. 1 accordingly is a dialysis system in one embodiment. System 10 includes a dialysate instrument 12, having a main portion 14 and a door or lid 16. Main portion 14 housing one or more pump actuator, one more valve actuator, a dialysis fluid heater and various sensors including an air detection sensor discussed in detail herein. Main portion 14 also houses a control system which can include a central processing unit ("CPU"), delegate controllers and safety controllers, each of which can have onboard processing and memory. The processing and memory on one of the controllers, such as a sensor board, monitors signals from the various sensors of instrument 12. One of the sensors again is an air detection sensor. Processing, memory and the dedicated software algorithm monitors the signal from the air detection sensor to look for air in the system.

It is contemplated to provide one or more air trap in the disposal set of the dialysis system which traps air, preventing same from reaching the patient or from being delivered from the patient to drain. Even so, an air detection sensor and method needs to be provided with instrument 10 to ensure that the one or more air trap is working properly. If air is sensed in a to-patient line for example, the processing and memory are configured to shut down the pumping of the fluid to the patient and to sound an alert or alarm. Similarly, in HD if air is sensed in dialysate running to the dialyzer, system 10 shuts down the dialysate pump and alarms. Or, if air is sensed in the patient's blood, system 10 stops the blood pump and sounds an alarm.

System 10 further includes a video screen 18 which displays information to the patient. System 10 further includes controls 20 which allow the patient to control instrument 12 of system 10. In the illustrated embodiment, instrument 12 operates with a disposal cassette 30 which can include, among other items, a pump chamber 32, dialysis heating fluid pathway 34, valve chamber 36 and tubing port 38 which attaches sealingly to flexible tubes such as a patient tube 40 and supply tubes 42. Cassette 30 and instrument 12 of system 10 can have additional features and are not limited to the features just described.

FIG. 1 shows that air sensing apparatus 50 of the present disclosure can be used with system 10 and instrument 12 in at least three configurations. Apparatus 50 refers collectively to apparatuses 50a to 50c of FIG. 1. Apparatus 50a is a standalone apparatus that includes a housing 52 configured to releasably hold patient tube 40. Housing 52 includes an air detection sensor, such as an ultrasonic air detection sensor, including an emitter and a receiver. Standalone housing 52 can include feet or insulating members 56 of housing 52 of standalone apparatus 50a to rest on a table or elsewhere as desired by the patient. Apparatus 50b includes clips 54 attached to main portion 14 of instrument 12. Clips 54 and clip housing 52 of air sensing apparatus 50b hold the associated air detection sensor and releasably secured patient tube 40 against the main portion 14 of instrument 12. Clips 54 also hold housing 52 of apparatus 50b releasably against main portion 14 of instrument 12.

Further alternative air sensing apparatus 50c integrates the air detection sensor within main portion 14 of instrument 12. Here, housing 52 of apparatus 50c is part of or integrated with the housing of main portion 14 and, if needed, the lid 16 of instrument 12.

Figure 2:
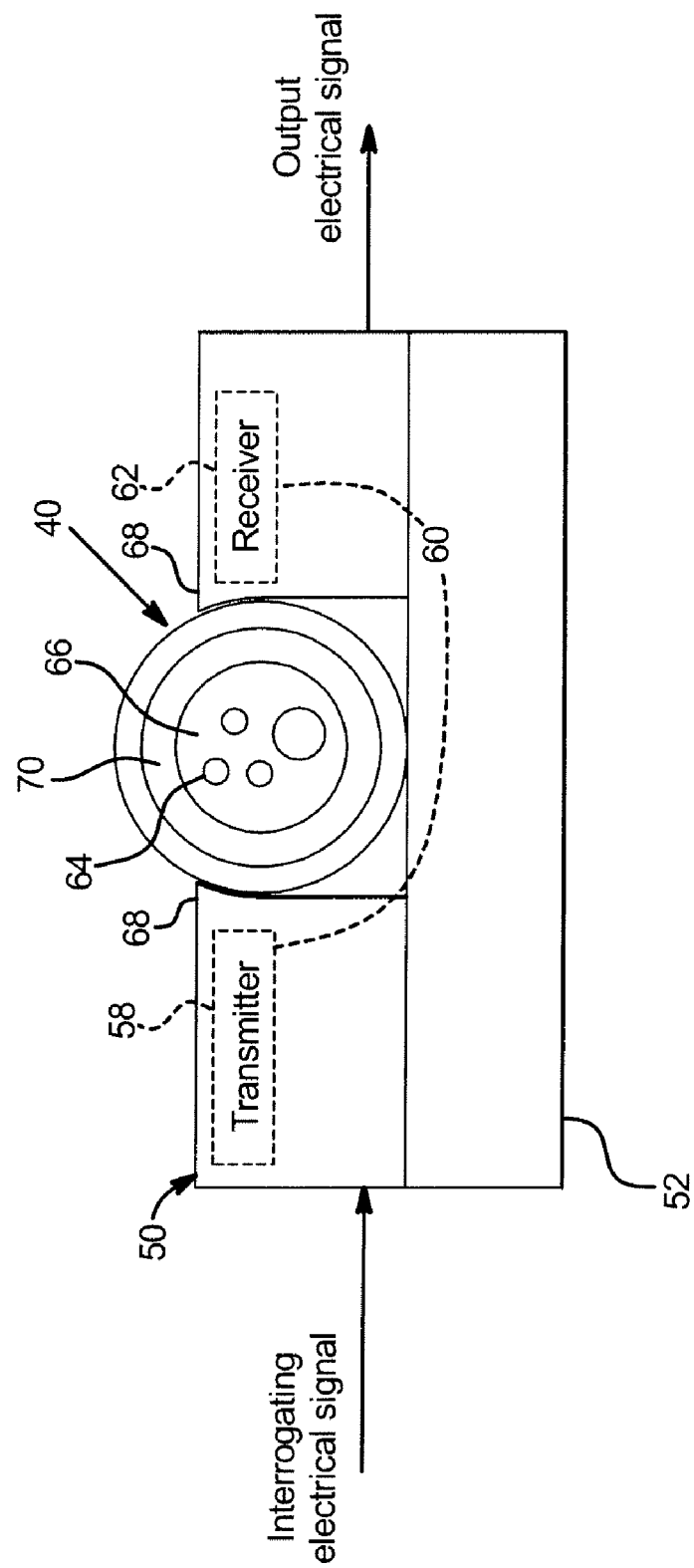
FIG. 2 is a cross sectional view of one embodiment of the air sensing apparatus and method of the present disclosure in a stand-alone configuration.

Referring now to FIG. 2, air sensing apparatus 50 representing any of the mounting configurations 50a to 50c of FIG. 1 is illustrated. Apparatus 50 includes housing 52 which holds an air detection transmitter 58 and air detection receiver 62 of an air detection sensor 60 in a proper position relative to a medical fluid conduit such as patient tube 42. Sensor 60 senses any air bubbles 64 that may be entrained in fluid 66. As seen, housing 52 holding transmitter 58 and receiver 62 includes apparatus 68, such as a clip or retaining ring, that releasably holds conduit 40 in place.

Sensor 60 in one embodiment is an ultrasonic sensor, which includes an ultrasonic transmitter 58 and an ultrasonic receiver 62. Transmitter 58 and receiver 62 can be piezo based transducers, known to those of skill in the art. One suitable ultrasonic sensor for sensing air in dialysate or blood is an ultrasonic sensor provided by Zevex company of Salt Lake City, Utah.

It has been found that the above-described sensor 60 has difficulty sensing air bubbles 64 within liquid 66 that are less than one millimeter diameter. Apparatus 50 however places a diameter reducing obstructer 70, having similar acoustical properties to 40, at a portion of conduit or patient tube 40 that is grasped and sensed via sensor 60 within housing 52. In one embodiment, obstructer 70 includes a same cross-sectional shape as does tube or conduit 40. For example, in the illustrated embodiment both tube 40 and obstructer 70 have a circular cross section. Alternatively, the conduit 40 and the obstructer 70 can have a different cross-sectional shape, such as square or rectangular.

In one embodiment, obstructer 70 press fits or has an interference fit within patient tube 40 and is located at a convenient or suitable position along tube 40 for mounting in housing 52 of apparatus 50a, 50b or 50c, whichever is employed. For example, obstructer 70 can have an outer diameter that is slightly larger than an inner diameter of patient tube or conduit 40. A suitable medically safe adhesive or solvent can be used additionally or alternatively for the press fit.

In one embodiment, the inner diameter of obstructer 70 is 50% of the inner diameter of conduit tube 40. Further, in one embodiment the cross-sectional area of obstructer 70 consumes 75% amount of the cross-sectional area of the inner diameter of tube 40. At the sensing portion, obstructer 70 can increase the wall thickness of the combined tubing structure from about 2 millimeters to about 3 millimeters.

It has been found that the above-described obstructer 70 has made the detection of air bubbles less than one millimeter and indeed the detection of air bubbles down to 400 micron significantly more effective. The thickened and reduced diameter sensing portion in combination with faster sample rates further increase the ability of apparatus 50 operating with the memory and processing of instrument 12 to detect smaller and smaller air bubbles.

Referring now to FIGS. 3A and 3B, alternative embodiments for providing a reduced inner diameter and/or increased wall thickness sensing portion for increasing the ability to sense smaller air bubbles are shown. In FIG. 3A, a smaller tube 70 is spliced between conduit portions 40. Here, housing 52 is sized and configured to releasably secure the smaller diameter tube segment 70. The wall thickness of patient tube 40 is not thickened, however the inner diameter of tubing 40 is reduced to tube segment 70.

FIG. 3B illustrates a further alternative embodiment, in which tubing 40 is extruded or otherwise formed to have a reduced diameter area 70 which is sensed at sensor 60. Here, the wall thickness of tubing 40 is increased, while inner diameter of tubing 40 is likewise decreased.

Figure 4:
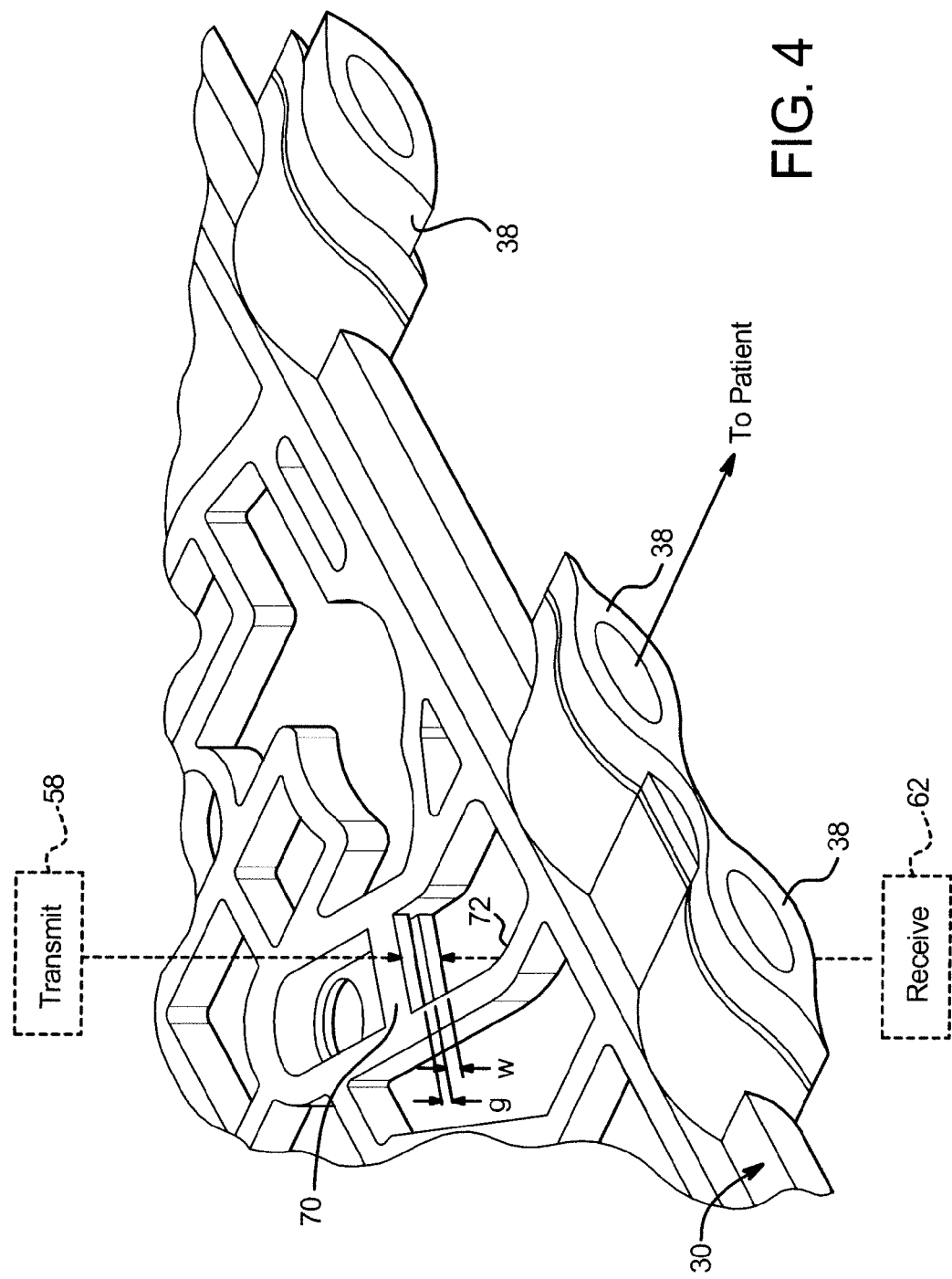
FIG. 4 illustrates one embodiment of a disposable cassette-based air sensing apparatus of the present disclosure.

Referring now to FIG. 4, a cassette-based apparatus 50d illustrates a further alternative configuration for the air sensing apparatus of the present disclosure. Here, transmitter 58 is mounted in one of main portion 14 or lid 16 of dialysis instrument 12, while the receiver 62 is mounted in the other of main portion 14 or lid 16. Transmitter 58 and receiver 62 of sensor 60, such as an ultrasonic sensor 60, are positioned to sense a portion 70 of dialysis cassette 30 leading, for example, to port 38 attached to patient tube 40. Thus, in the illustrated example, sensing area 70 is positioned just prior to when the solution is about to leave cassette 30 to be pushed through the patient tube to the patient. This is a desirable position because the air can be captured in time and pumped to drain, however, the dialysis fluid is sensed sufficiently downstream that air generated due to fluid heating located upstream of sensing area 70 is detected.

As illustrated, sensing area 70 reduces a cross-sectional area of cassette flow path 72. In an embodiment, sensing area 70 of cassette 30 is formed of the same rigid material and during the same formation process that is used to create the fluid pathways such as pathway 72, the fluid ports 38 and the valve chambers 36 (shown in FIG. 1). The manufacturing process for cassette 30 can be controlled precisely to achieve a sensing gap thickness g and wall thickness w, determined to be the best for detecting small air bubbles.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid air detection apparatus comprising:
   an emitter;
   a receiver;
   a housing configured to hold at least a portion of a medical fluid conduit between the emitter and the receiver; and
   wherein the medical fluid conduit includes a narrowed inner diameter at the medical fluid conduit portion that forces flow of medical fluid through the narrowed diameter, the narrowed diameter configured to enhance the ability of the emitter and the receiver to detect air bubbles having a diameter of less than one millimeter, the conduit at the portion including an obstruction that increases a wall thickness of the conduit to produce the narrowed inner diameter.

2. The medical fluid air detection apparatus of claim 1, wherein the obstruction is press-fit or interference fit within the medical fluid conduit.

3. The medical fluid air detection apparatus of claim 1, wherein the medical fluid conduit is a tube, the obstruction wedged into the tube at the portion of the medical fluid conduit.

4. The medical fluid air detection apparatus of claim 1, wherein the obstruction includes an inner diameter that is at least 50 percent less than an inner diameter of the medical fluid conduit.

5. The medical fluid air detection apparatus of claim 1, wherein the obstruction has a cross-sectional area that consumes at least 75 percent of a cross-sectional area of the portion of the medical fluid conduit.

6. The medical fluid air detection apparatus of claim 1, wherein the emitter and receiver operate acoustically.

7. The medical fluid air detection apparatus of claim 1, wherein the housing is one of: (i) configured to be attached to a dialysis instrument; (ii) a housing of a dialysis instrument; and (iii) a stand-alone housing.

8. The medical fluid air detection apparatus of claim 1, wherein the housing includes a retainer that grasps the medical fluid conduit.

9. The medical fluid air detection apparatus of claim 1, wherein the portion of the medical fluid conduit includes at least one end configured to seal to a flexible tube.

10. The medical fluid air detection apparatus of claim 1, wherein the portion of the medical fluid conduit is a portion of a medical fluid pumping cassette, the conduit a to-patient conduit extending from the pumping cassette.

11. The medical fluid air detection apparatus of claim 1, wherein the conduit is a first conduit, the emitter and receiver are a first emitter and a first receiver, and which includes a second conduit, second emitter and second receiver, the second conduit including a narrowed inner diameter configured to force medical fluid to flow through the narrowed inner diameter at a portion of the conduit operating with the second emitter and the second receiver.

12. The medical fluid air detection apparatus of claim 11, wherein the first conduit is a medical fluid supply conduit and the second conduit is a to-patient conduit.

13. A medical fluid air detection apparatus comprising:
   an air detection sensor;
   a medical fluid conduit including a narrowed inner diameter configured to (i) force medical fluid to flow through the narrowed inner diameter at a portion of the conduit operating with the sensor, and (ii) enhance the ability of the sensor to detect air bubbles having a diameter of less than one millimeter;
   an internal obstruction located at the portion of the narrowed diameter, and increasing a wall thickness of the conduit to produce the narrowed inner diameter, the obstruction including an inner diameter that is at least 50 percent less than an inner diameter of the medical fluid conduit.

14. The medical fluid air detection apparatus of claim 13, wherein at least one of: (i) the sensor is an acoustical sensor; (ii) the sensor includes an emitter and a receiver; and (iii) the apparatus includes a housing configured to hold the medical fluid conduit adjacent to the sensor.

15. The medical fluid air detection apparatus of claim 13, wherein the internal obstruction is press-fit or interference fit within the medical fluid conduit.

16. A medical fluid air separation method comprising:
   forcing a medical fluid to flow within a narrowed portion of a medical fluid conduit;
   detecting air bubbles within the medical fluid flowing through the narrowed portion, the narrowed portion enhancing the ability of the sensor to detect air bubbles having a diameter of less than one millimeter within the medical fluid flowing through the narrowed portion; and
   contacting an internal surface of the medical fluid conduit with a smaller diameter conduit to increase a wall thickness of the medical fluid conduit and to create the narrowed portion, the smaller diameter conduit being at least 50 percent less than an inner diameter of the medical fluid conduit.

17. The medical fluid air separation method of claim 16, wherein the internal surface of the medical fluid conduit is a tubing surface or a cassette fluid path surface.

18. The medical fluid air separation method of claim 16, which includes press-fitting or interference fitting the smaller diameter conduit within the medical fluid conduit to create the narrowed portion.

19. A medical fluid air detection apparatus comprising:
an emitter;
a receiver;
a housing configured to hold at least a portion of a medical fluid conduit between the emitter and the receiver, the portion of the medical fluid conduit is a medical fluid conduit residing within a medical fluid pumping cassette, the housing a housing of a dialysis instrument configured to accept the cassette; and
wherein the medical fluid conduit includes a narrowed inner diameter at the medical fluid conduit portion that forces flow of medical fluid through the narrowed diameter, the narrowed inner diameter configured to enhance operation of the emitter and the receiver, the conduit at the portion including an internal obstruction press-fit or interference fit into the conduit that increases a wall thickness of the conduit to produce the narrowed inner diameter.

* * * * *